United States Patent [19]

Bishop et al.

[11] Patent Number: 5,496,702

[45] Date of Patent: Mar. 5, 1996

[54] IMMUNOASSAY ELEMENTS HAVING STABLE LEUCO DYE COATINGS

[75] Inventors: John F. Bishop; Linda A. Mauck, both of Rochester, N.Y.

[73] Assignee: Johnson & Johnson Clinical Diagnostics, Inc., Rochester, N.Y.

[21] Appl. No.: 299,729

[22] Filed: Sep. 1, 1994

[51] Int. Cl.[6] .................................................... G01N 33/53
[52] U.S. Cl. ......................... 435/7.9; 435/7.92; 435/7.93; 435/7.94; 435/7.95; 435/25; 435/28; 435/962; 435/969; 435/970; 436/531; 436/810; 427/2.11; 422/56; 422/57
[58] Field of Search .................. 427/2, 2.11; 422/56–57; 435/7.9, 7.92–7.95, 25, 28, 962, 969, 970; 436/531, 810

[56] References Cited

U.S. PATENT DOCUMENTS

| | | | |
|---|---|---|---|
| 4,552,654 | 6/1985 | Chisvette et al. | 106/288 |
| 4,587,211 | 5/1986 | Ishida et al. | 430/619 |
| 4,703,002 | 10/1987 | Findlay et al. | 435/17 |
| 5,024,935 | 6/1991 | McClune et al. | 435/7.1 |
| 5,074,887 | 12/1991 | Koci | 8/527 |
| 5,155,024 | 10/1992 | Eikenberry | 435/7.9 |
| 5,200,315 | 4/1993 | Sutton et al. | 435/6 |
| 5,358,852 | 10/1994 | Wu | 435/7.94 |

*Primary Examiner*—Carol A. Spiegel

[57] ABSTRACT

An immunoassay element comprising at least one layer containing a leuco dye coating composition comprising:

| Component | | Dry Weight Ratio (Range) |
|---|---|---|
| a) | Triarylimidazole leuco dye | 55–80 |
| b) | Antioxidant | 7–40 |
| c) | Poly[poly(ethylene oxide)-block-poly(propylene oxide)] nonionic block copolymer | 6–20 |
| d) | Alkylaryloxypoly(alkylene oxide) nonionic surfactant | 1–16 |

7 Claims, No Drawings

IMMUNOASSAY ELEMENTS HAVING STABLE LEUCO DYE COATINGS

FIELD OF THE INVENTION

This invention relates to clinical chemistry. More particularly it relates to immunoassay elements containing leuco dye coatings and to methods of using such elements.

BACKGROUND OF THE INVENTION

Various dry analytical assay elements are commercially available, such as Kodak's Ektachem Clinical Chemistry slides, and certain known dry multilayer immunoassay elements, include a layer comprising a leuco dye. In the course of an assay for a specified analyte in a sample, the leuco dye, in the presence of hydrogen peroxide and a material having peroxidase activity, is oxidized to a colored form. As is well known the reflection density of the color is proportional to the concentration of analyte in the sample. The reflection density can be measured using a reflectometer. See U.S. Pat. Nos. 4,670,385; 4,089,747; 5,024,935; 4,089,747 and 4,258,001 for further details and references to other literature describing this art.

Typical leuco dyes used for this purpose are highly aromatic leuco dyes that cannot be dissolved and deposited or coated as an aqueous solution. Such leuco dyes are the diaryl- and triarylmethanes of U.S. Pat. No. 4,670,385; and the diaryl- and triarylimidazole dyes of U.S. Pat. No. 4,089,747 and U.S. Pat. No. 5,024,935. Such dyes have been coated as dispersions by dissolving the dye in an organic solvent (methanol or dimethyl sulfoxide) and reprecipitating in an aqueous polymer solution to produce a coating composition of the dye in a polymer solution; or dissolving the dye in a "coupler solvent" (diethyl lauramide) and redispersing the coupler solvent solution in an aqueous solution.

Another process for making such dye coating compositions is to dissolve the dye in a good solvent for the dye (dimethyl sulfoxide), and reprecipitate the dye in an aqueous coating composition. This requires very careful control of the precipitation process in order to optimize the particle size of the dye in the coating composition. This is difficult to do because the process is sensitive to stir rate and rate of addition of the dye solution, thus large particles are formed, and consequently more dye than necessary must be employed for adequate color formation in an assay. Further, the process is unpredictably irreproducible, because, in addition to the above, the dye tends to coagulate, and the coating composition has limited shelf life. It is also desirable to avoid the use of DMSO.

There is a great need for immunoassay elements comprising stable leuco dye coating compositions form without use of organic solvents, that use of up to half as much dye, are reproducible, and do not require stringent process control operations.

SUMMARY OF THE INVENTION

The present invention provides an immunoassay element comprising at least one layer containing a leuco dye coating composition comprising:

| Component | Dry Weight Ratio (Range) |
| --- | --- |
| a) Triarylimidazole leuco dye | 55–80 |
| b) Antioxidant | 7–40 |
| c) Poly[poly(ethylene oxide)-block-poly(propylene oxide)] nonionic block copolymer | 6–20 |
| d) Alkylaryloxypoly(alkylene oxide) nonionic surfactant | 1–16 |

The present invention also provides a method for the assay of immunologically reactive ligand in an aqueous liquid sample. The method comprises the steps of:

A. providing a dry immunoassay analytical element according to the present invention wherein the labeled ligand is an enzyme labeled ligand;

B. contacting a finite area of the layer comprising the enzyme labeled ligand with a sample of the liquid sample thereby forming at least one of (i) an immobilized ligand-receptor complex and (ii) an immobilized enzyme labeled ligand-receptor complex;

C. contacting the finite area of the layer comprising the enzyme labeled ligand with a substrate solution thereby catalyzing the development of a color; and D. determining the concentration of the ligand colorimetrically.

DETAILS OF THE INVENTION

Stable, reproducible coating compositions of the triarylimidazole leuco dyes, can be prepared by the process of this invention. The process does not require dissolution of the dye in any organic solvents. The process is carried out (1) in the presence of a combination of two nonionic surface-active agents, one of which is an alkylene oxide block copolymer, (2) an antioxidant to protect the dye, and (3) a suitable grinding media.

More particularly, the new process comprises the steps of:

1. Blending a mixture of:

| Component | Approximate Preferred Amt (%) Wet | Approximate Preferred Amt (%) Dry | Range (%) Wet | Range (%) Dry |
| --- | --- | --- | --- | --- |
| a) Triarylimidazole Leuco Dye | 5 | 66.4 | 4–6 | 55–80 |
| b) Antioxidant (preferably Dimedone) | 1.25 | 16.7 | 1–1.5 | 7–40 |
| c) Poly[poly(ethylene oxide)-block-poly(propylene oxide)] nonionic block copolymer surfactant | 0.90 | 12.0 | 0.7–1.1 | 6–20 |
| d) Alkylaryloxypoly(alkylene oxide) nonionic surfactant | 0.37 | 4.9 | 0.3–0.45 | 1–16 |
| e) Water | 92.47 | — | Balance | — |

2. Milling an aqueous slurry of the mixture prepared in step 1 with a milling media and conventional milling apparatus and procedures such as ball milling, media milling, attritor milling, or vibratory milling. The volume/volume ratio of the mixture to be milled and the milling media ranging from about 3:1 to 1:3, preferably being close to 1:1. The milling media has an average diameter of less than about 4 mm, and preferably of about 0.3 to 2.0 mm. Milling is carried out until the average particle size of the leuco dye is reduced to about 0.01 to 4.0 mm, more preferably about 0.01 to 2.0 μm, and most preferably about 0.05 to 0.5 μm.

Milling times can require from 1 to 20 days in low energy milling procedures such as those using ball milling and vibratory milling; however, the more energetic media mills and attritor mills require less treatment time. They can achieve size reduction comparable to that obtained in 1 to 20 days with a ball mill, in only several minutes to several hours.

3. Separating the milling media from the resulting dye coating composition, preferably by screening through a screen having openings of about 0.1 to 0.2 mm.

The above process provides new dry coating compositions that are useful dry multilayer analytical elements. The coating compositions comprise:

| Component | | Dry Weight Ratio (Range) |
|---|---|---|
| a) | Triarylimidazole leuco dye | 55–80 |
| b) | Antioxidant | 7–40 |
| c) | Poly[poly(ethylene oxide)-block-poly(propylene oxide)] nonionic block copolymer | 6–20 |
| d) | Alkylaryloxypoly(alkylene oxide) nonionic surfactant | 1–16 |

The ratios given in this table are relative to only the components in the table. These coating compositions may also comprise a vehicle such as gelatin and a hardener, and optionally other conventional addenda such as a buffer and other surfactants.

The milling process is a fragmentation process operated in water using a combination of two nonionic surfactants that stabilize the resulting aqueous coating composition. The surfactant/stabilizer components employed maintain coating composition stability against settling and flocculation of both the dye and the antioxidant allowing each dispersed component to exist as discrete particles in the coating composition without aggregation or flocculation.

One of the surfactants is a nonionic block copolymer comprising blocks of two different poly(alkylene oxides), preferably blocks of a straight-chain poly(alkylene oxide) such as poly(ethylene oxide) and blocks of a branched chain poly(alkylene oxide) such as poly(propylene oxide), and most preferably is a poly[poly(ethylene oxide)-block-poly(propylene oxide)] copolymer. This surfactant is essential to colloidally stabilize the leuco dye both during the milling process and in the coating composition. Such polymers are commercially available, for example, from BASF under both the PLURONIC-AND-TETRONIC tradenames, from Rhone-Poulenc under the ANTAROX tradenames, from Witco Corp. under the ARNOX-BF-Series tradenames, from PPG Industries under the MACOL tradenames, from Olin Corp. under the POLY-TERGENT tradenames, and from others. The preferred block copolymer is TETRONIC 908, a poly[poly(ethylene oxide-block-poly(propylene oxide)] copolymer sold by BASF.

The other surfactant is a nonionic alkylaryloxypoly(alkylene oxide) wherein each alkyl group has about 6 to 16 carbon atoms (octyl, isooctyl, nonyl, or isononyl); the aryl group is preferably phenyl or alkyl substituted phenyl having one or two additional alkyl substituents. This surfactant is essential to colloidally stabilize the antioxidant in the milling composition and in the coating composition. The related alkyl groups have 1 to 16 carbon atoms. The alkylene portion of the alkylene oxide polymer is a straight or branched alkylene group of 2 to 4 carbon atoms. Alkylene may be substituted with hydroxyl groups; and the number of polymerized alkylene oxide groups per molecule averages about 5 to 30, preferably 5 to 15, and most preferably about 10. The preferred surfactant is an isononylphenoxypoly(glycidol) having about 10 recurring polymerized glycidol units available from Olin Chem Co. under the tradename SURFACTANT 10G. Other suitable materials are available from Union Carbide under the TRITON tradenames, from Witco Corp. under the ARNUL and DESONIC tradenames, from Texaco Chem Co. under the SURFONIC tradenames, and from others.

An antioxidant is present in the dye coating composition of this invention to prevent oxidation of the dye (unwanted color formation) during and after the milling process as well as during storage of the finished analytical elements. The preferred antioxidant is dimedone. Other suitable antioxidants are 4'-hydroxyacetanilide and derivatives thereof having electron withdrawing groups on the 3'-, 5'-or both positions, the naphthalene analogues thereof, hydroquinones and aminophenols.

Fragmentation is accomplished using a grinding media in a conventional grinding process such as ball milling, media milling, attritor milling and vibratory milling. The grinding media are generally spherical particles of less than about 4 mm average diameter, and preferably about 0.3 or more to about 2.0 mm average diameter. Suitable milling media include particles of glass, ceramics (such as titania, zirconia, and alumina), plastics, metals (such as steel, silicon nitride, and tungsten carbide), sand, and others known in the art. Glass and ceramic beads are preferred. Zirconium oxide is useful Ball milling is conducted by charging a cylindrical vessel with enough grinding media to fill about half the volume of the vessel with beads. A slurry of the dye mixture is added to the vessel so that 25 to 100% of the slurry volume resides in the interstices of the grinding media. Preferably about 75% of the slurry volume resides in the media voids, and about 25% is above the grinding media as the "supernatant." The vessel is closed and rotated concentrically about its axis at about 10 to 90% of the "critical speed." The 100% critical speed is the rotational speed at which the grinding media begins to centrifuge against the vessel wall and is no longer able to cascade freely as the vessel rotates. A rotational speed of about 40 to 70% of the critical speed generally provides maximum grinding efficiency and is thus preferred.

Milling is terminated when the desired particle size is achieved. Particle size is determined by removing a sample, separating the dye coating composition from the grinding media, and measuring the average particle size of the leuco dye by conventional sizing methods such as by light scattering measurements or disk centrifugation.

The milling media is separated from the dye coating composition by conventional screening methods that retain the grinding beads and allow collection of the dye coating composition of dye and antioxidant.

As stated previously, the coating compositions are useful in multilayer dry analytical elements, particularly immunoassay elements. The elements can be single or multilayer or a combination of layers having zones within such layers. In general the elements can comprise a radiation transmissive support, one or more reagent layers, a particulate spreading layer, and in some embodiments, a receptor layer between the reagent layer(s) and the spreading layers. The receptor layer or the spreading layer contain receptor beads upon which antibodies are immobilized.

The layers can be coated using well known coating techniques in this art. For example slide-extrusion hoppers of the type described in U.S. Pat. No. 2,761,417 are often advantageous for simultaneous coating of a plurality of layers at least one of which is comprised of polymeric particles bearing immobilized antibody beads. More particularly, a multilayer element can be coated by directing a coating composition containing the beads through an extrusion slot of a slide extrusion hopper and simultaneously flowing a layer of a second coating composition, which, if desired, may also contain beads down a slide surface of the slide-extrusion hopper.

The particulate layer in which the antibodies are immobilized is porous. Materials for use in such layers are well known in the art of making dry analytical elements. A preferred particulate layer is a bead spreading layer (BSL). This layer can be easily constructed to have suitable porosity for use in the elements of the present invention to accommodate a test sample (e.g. 1 to 100 mL), diluted or undiluted. Preferably, the spreading layer is isotropically porous, which property is created by interconnected spaces between the particles comprising the zone. By isotropically porous is meant that the spreading layer uniformly spreads the applied fluid radially throughout the layer.

Useful particulate spreading layers, including bead spreading layers are disclosed in U.S. Pat. Nos. 4,670,381; 4,258,001 and 4,430,436.

The particulate layer of the element is carried on a suitable support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

The element can comprise one or more additional layers, e.g. separate or combined reagent/spreading layer and a gelatin/buffer layer containing other necessary additives, coupling enzymes, etc.

The gelatin/buffer layer or the reagent layer or the spreading layer of the element can contain the indicator composition comprising one or more reagents dispersed in one or more synthetic or natural binder materials, such as gelatin, or other naturally-occurring colloids, homopolymers and copolymers, such as poly(acrylamide), poly(vinyl pyrrolidone), poly(N-isopropylacrylamide), poly(acrylamide-co-N-vinyl-2-pyrrolidone) and similar copolymers.

Other optional layers, e.g. subbing layers, radiation-blocking layers, etc. can be included if desired. All layers of the element are in fluid contact with each other, meaning that fluids and reagents and uncomplexed reaction products in the fluids can pass between superposed regions of adjacent layers.

The layers of the element can contain a variety of other desirable but optional components, including surfactants, thickeners, buffers, hardeners, antioxidants, coupler solvents, and other materials known in the art. The amounts of these components are also within the skill of a worker in the art.

The elements can be used to determine low concentrations of immunologically reactive ligands in a liquid, such as a biological fluid (e.g., whole blood, serum, plasma, urine, spinal fluid, suspensions of human or animal tissue, feces, saliva, lymphatic fluid and the like). The ligands can be determined at concentrations as low as about $10^{-11}$ molar, and most generally at a concentration of from about $10^{-10}$ to about $10^{-4}$ molar.

Ligands which can be so determined, either quantitatively or qualitatively, include therapeutic drugs (e.g., phenobarbital, digoxin, digitoxin, theophylline, gentamicin, quinidine, phenytoin, propanolol, carbamazepine, tobramycin, lidocaine, procainamide and the like), natural or synthetic steroids (e.g., cortisol, aldosterone, testosterone, progesterone, estriol, etc.), hormones (e.g., thyroid hormones, peptide hormones, insulin, etc.), proteins (e.g. albumin, IgG, IgM, ferritin, blood clotting factors, C-reactive protein, isoenzymes, apolipoproteins, etc.), antigens, antibodies including monoclonal antibodies, and other species which will naturally react with a receptor. This invention is particularly useful for the determination of therapeutic drugs, such as digoxin, phenytoin, theophylline, or phenobarbital and hormones such as thyroxine or triiodothyronine.

The assay can be competitive or a sandwich assay. It can be carried out using any suitable label which can be attached to analyte derivatives or antibodies (as used in sandwich assays). Useful labels include radioactive tags, dyes, fluorescers, enzymes, enzyme substrates, enzyme inhibitors, allosteric effectors, cofactors and other known enzyme modulators. Enzymes, such as glucose oxidase, peroxidases such as horseradish peroxidase and amine-enriched horseradish peroxidase, alkaline phosphatase and galactosidase are preferred labels.

When an enzyme label is used, the substrate for the enzyme is present in the element or added thereto in the developing liquid. The substrate can be added to the element prior to or simultaneously with the liquid sample, or after completion of the binding reaction. It is within the skill of the ordinary worker in clinical chemistry to determine a suitable substrate for a given label. The substrate can be a material which is directly acted upon by the enzyme label, or a material that is involved in a series of reactions which involve enzymatic reaction of the label. For example, if the enzyme label is a peroxidase, the substrate is hydrogen peroxide. Using glucose oxidase as an example, the substrate glucose is generally present in the reagent layer or is added in the developing liquid to yield about 0.01 moles/m$^2$, and preferably from about 0.001 to about 0.1 mole/m$^2$. A worker skilled in the art would know how to adjust the amount of a particular substrate for the amount of enzyme label used in the assay.

The indicator composition comprises a leuco dye coating composition provided by this invention. That is the composition includes a leuco dye and peroxidase or another suitable peroxidative compound which generates a detectable dye as a result of the formation of hydrogen peroxide produced, for example, when glucose oxidase converts glucose to gluconic acid, is contained in or supplied to the composition during the assay.

The immunoassay can be manual or automated. In general, the amount of a ligand in a liquid is determined by taking the element from a supply roll, chip packet or other source and physically contacting a finite area of the spreading layer with a sample of the liquid, e.g. 1 to 100 mL. The finite area which is contacted is generally no more than about 150 mm$^2$.

The amount of ligand is determined bypassing the element through a suitable apparatus for detecting the complexed ligand analog directly or the detectable species formed as a result of enzymatic reaction of an enzyme label and a substrate. For example, the species can be detected with suitable spectrophotometric apparatus using generally known procedures. In an enzymatic reaction, the resulting product is determined by measuring, for example, the rate of change of reflection or transmission density in the finite area which was contacted with the test sample. The area which is measured is generally from about 5 to about 25 mm$^2$. The amount of ligand in the liquid sample is inversely proportional to the amount of label measured in the finite area. Generally, label measurement is made after application of a substrate solution.

Especially useful immunoassay elements are disclosed in U.S. patent application 08/260,939 filed Jun. 16, 1994 by Sutton et al. This application is expressly incorporated herein by reference. This case discloses a dry immunoassay analytical element, for assaying a ligand, comprising in the following order, (a) a layer containing a labeled ligand, (b) a bead spreading layer, c) a cross-linked hydrophilic polymer layer and d) a support; wherein (i) a fixed concentration of an immobilized receptor for the labeled ligand is located in a zone (receptor zone) at the interface of layers (b) and (c); and (ii) the receptors are immobilized by being covalently bonded to polymeric beads that are smaller than the beads in layer (b).

The dry leuco dye coating composition provided by the present invention is especially useful when incorporated into the receptor zone thereof or in the spreading layer.

The labeled ligand is gravure coated to 1) minimize wet coverage of the labeled ligand coating composition, to avoid precontact of the labeled ligand with the receptor, while at the same time maintaining enough wetness to achieve uniform coverage of the labeled ligand and 2) and achieve rapid drying in a way that a) removes substantially all of the coating solvent; b) avoids adversely affecting the porosity of the spread layer and spreading time and c) maintains sufficient enzyme activity.

The relative affinity of antibody and labeled ligand for each other is also an important factor in minimizing prebinding. This factor is controlled, as is well known by those skilled in this art, by manipulating the structure of the labeled ligand together with a prudent choice of antibody.

In general the level of coated labeled ligand coverage needed in an element is determined empirically for each specific immunoassay according to the following procedure:

1. Determine the concentration of labeled ligand needed to achieve acceptable immunoassay performance when the immunoassay is performed by contacting the analytical element with the labeled ligand concurrently with a sample. Acceptable assay performance is achieved when (a) the assay can be carried out in less than 20 minutes; (b) the dynamic range of the assay is such that the minimum and maximum ligand concentrations detectable cover a clinically useful concentration range; and (c) clinically significant ligand concentrations can be detected across the dynamic range.

2. Empirically determine the level of coated labeled ligand coverage needed with the same analytical element to achieve the above established acceptable assay performance by:

A. Coating, directly over the particulate receptor zone of the element used to establish optimum spotted labeled ligand levels, the labeled ligand at a coverage in g/m$^2$ that is some fraction, multiple or the same as the concentration of labeled ligand used in spotting the labeled ligand in 1, supra.

B. Conduct a series of assays with test samples containing a known concentration of the ligand.

C. Compare the results of the assays with the known concentration of ligand; and D. Repeat steps B and C as needed, varying the labeled ligand coverage according to the results seen in step 2C to determine the labeled ligand coverage required.

Depending on the labeled ligand, the coverage of the labeled ligand could be less than, the same or several multiples greater (2X, 3X, 4X, etc.) than the labeled ligand concentration needed when the same assay is carried out by spotting the labeled ligand directly on the analytical element.

Using the above guidelines, carefully controlled gravure coating procedures were successfully carried out using the following coverages and drying protocols. The labeled ligand coatings in the elements of the invention were prepared with a gravure machine (made by Yasui of Japan). Drying conditions are generally about 120° F. (49° C.) in the first drying section only. The second section was not used. A typical gravure cylinder used contained 295 cells/inch (1.344×10$^8$ cells/m$^2$). The cells had a depth of 19 microns, a width of 72 microns and a land width between cells of 12 microns. This cylinder will deliver about 4.3 g/m$^2$ of coating composition containing the labeled ligand to the bead spreading layer using the direct gravure process at a coating machine speed of 50 ft/min (15.24 m/minute). Other gravure cylinders can deliver from about 2.5 to 6.8 g/m$^2$ of coating solution. Those skilled in the gravure coating arts will be readily able to adapt the previously described procedure to any gravure coating machine. The coating composition for the labeled ligand was as follows:

| Coated Labeled Ligand Coating Composition Based on 4.3 g/m$^2$ Wet Coverage | |
| --- | --- |
| Component | g/m$^2$ Dry Coverage |
| MOPS Buffer | .0045 |
| BSA (Bovine Serum Albumin) | .000215 |
| poly(acrylamide) | .00108 |
| 4'-Hydroxyacetanilide | .000325 |
| *Labeled ligand | .000016 |

*Labeled ligand has been coated anywhere between 4 and 64 μg/m$^2$

The remaining layers of the element can be coated using well known coating techniques in this art. However each layer is coated separately and allowed to dry before application of subsequent layers.

The layers forming the elements used in the following examples were prepared using the following procedure. Each layer was dried before it was overcoated with another layer.

1. Coating a cross-linked gelatin layer on subbed poly(ethylene terephthalate) support. The coating composition contained gelatin and an electron transfer agent [e.g., 4'-hydroxyacetanilide (4'-HA)], a buffer, surfactant, and a gelatin hardener.

2. Coating the receptor zone. The coating composition for the zone contains (a) an antibody for the analyte (ligand) immobilized on 0.1–5 μm polymer beads in a polymer and (b) a leuco dye coating composition provided by this invention. Optionally, the leuco dye can be incorporated instead in the bead spreading layer.

3. Coating the bead spreading layer over the dried receptor zone. The coating composition contained large (20–35 μm) polymer particles or beads [typically poly(vinyltoluene-co-methacrylic acid) (weight ratio 98/2) beads] adhered together with a latex polymer adhesive, preferably poly(methyl acrylate-co-sodium 2-acrylamido-2-methylpropane-sulfonate-co-2-acetoacetoxyethyl methacrylate) (weight ratio 90/4/6). The layer may include the leuco dye, an electron transfer agent, dimedone, a buffer, bovine serum albumin, and a surfactant.

4. A horseradish peroxidase, usually amine enriched horseradish peroxidase, labeled analyte composition is gravure coated on top of the bead spreading layer. The composition optionally can include an electron transfer agent (4'-HA), a buffer (MOPS), bovine serum albumin, and a hydrophilic polymer vehicle such as polyacrylamide.

The receptor zone must be coated with a polymer according to the group (I), (II), (III), (IV), (V) and (IV). However the zone in the finished element may be essentially free of the polymer. Some, none, or essentially all, of the polymer will migrate into the bead spreading layer (b) when layer (b) is coated over the receptor zone coating.

The receptor zone must be coated with a polymer selected from group consisting of (I), (II), (III), (IV), (V) and (VI) as follows:

(I) cross-linked polymers comprising about 30 to 97 weight percent of polymerized N-alkyl-substituted acrylamide monomers, about 3 to 25 weight percent polymerized crosslinking monomer having at least two addition polymerizable groups per molecule of crosslinking monomer, and 0 to 60 weight percent of other polymerized hydrophilic monomers (II) poly(vinyl alcohol);

(III) bovine serum albumin;

(IV) acacia gum;

(V) homopolymers of poly-N-vinylpyrrolidone having a molecular weight in the range 8000 to 400,000; and (VI) water-soluble vinyl addition copolymers having two or more monomers selected from the group consisting of acrylamide, methacrylamide, N-alkylsubstituted acrylamides, N-alkyl substituted methacrylamides, 1-vinylimidazole, 2-alkyl substituted-1-vinylimidazoles, 2-hydroxyalkyl substituted-1-vinylimidazoles, N-vinylpyrrolidone, hydroxyalkyl acrylates, hydroxyalkyl methacrylates, acrylic acid, sulfoalkyl acrylates, sulfatoalkyl acrylates, sulfoalkyl methacrylates, sulfatoalkyl methacrylates, N-sulfoalkylacrylamides, N-sulfatoalkylacrylamides, and N-sulfoalkylmethacrylamides, N-sulfatoalkylmethacrylamides, ethylenesulfonic acid and sulfo-substituted styrenes. The alkali metal (sodium, lithium, and potassium), and ammonium salts of the monomers containing sulfato- and sulfo- moieties are included in group (VI). Alkyl, wherever it appears in group (I) and (VI) monomers include 1 to 6 carbon atoms.

The receptor zone must be coated with a polymer according to the group (I), (II), (III), (IV), (V) and (IV). However the zone in the finished element may be essentially free of the polymer. Some, none, or essentially all, of the polymer will migrate into the bead spreading layer (b) when layer (b) is coated over the receptor zone coating.

Useful N-alkyl-substituted acrylamides for groups (I) and (IV) polymers include N-isopropylacrylamide, N-n-butylacrylamide, N,N-diethylacrylamide and N-n-propylacrylamide. This includes cross-linked polymers comprising from about 30 to 97 weight percent of a polymerized N-alkyl substituted acrylamide such as N-isopropylacrylamide. Polymers comprising 60 to 97 weight percent of polymerized N-isopropylacrylamide are used in the examples to clarify the utility of group (I) polymers.

Group (I) polymers also comprise from about 3 to 25 weight percent of one or more polymerized crosslinking monomers having at least two addition-polymerizable groups per molecule. These crosslinking monomers are generally well known in the art. The preferred crosslinking monomers contain acrylamido or methacrylamido groups to facilitate polymerization with the N-alkyl-substituted acrylamides.

Examples of useful crosslinking monomers for group (I) polymers are:
N,N'-methylenebisacrylamide;
N,N'-methylenebismethacrylamide;
ethylene dimethacrylate;
2,2-dimethyl-1,3-propylene diacrylate;
divinylbenzene;
mono[2,3-bis(methacryloyloxy)propyl] phosphate;
N,N'-bis(methacryloyl)urea;
triallyl cyanurate;
allyl acrylate;
allyl methacrylate;
N-allylmethacrylamide;
4,4'-isopropylidenediphenylene diacrylate;
1,3-butylene diacrylate;
1,4-cyclohexylenedimethylene dimethacrylate;
2,2'-oxydiethylene dimethacrylate;
divinyloxymethane;
ethylene diacrylate;
ethylidene diacrylate;
propylidene dimethacrylate;
1,6-diacrylamidohexane;
1,6-hexamethylene diacrylate;
1,6-hexamethylene dimethacrylate;
phenylethylene dimethacrylate;
tetramethylene dimethacrylate;
2,2,2-trichloroethylidene dimethacrylate;
ethylenebis(oxyethylene) diacrylate;
ethylenebis(oxyethylene) dimethacrylate;
ethylidyne trimethacrylate;
propylidyne triacrylate;
vinyl allyloxyacetate;
1-vinyloxy-2-allyloxyethane;
2-crotonoyloxyethyl methacrylate;
diallyl phthalate; and
2-(5-phenyl-2,4-pentadienoyloxy)ethyl methacrylate.

The group (I) polymer can include 0 to 60 weight percent of polymerized hydrophilic monomers. Amounts of 5 to 35 weight percent are also useful. In particular such monomers have one or more groups selected from hydroxy, pyrrolidone, amine, amide, carboxy, sulfo, carboxylate salt, sulfonate salt and sulfate salt groups. Generally the counter ions of the salt groups are alkali metal or ammonium. Useful hydrophilic monomers are acrylic acid and methacrylic acid and their salts, sodium 2-acrylamido-2-methylpropane sulfonate, 2-hydroxyethyl acrylate, 2-hydroxyethyl methacrylate; 2-hydroxypropyl acrylate, 2-hydroxypropyl methacrylate; o- and p-styrenesulfonic acid, potassium salt; p-styrenesulfonic acid, potassium salt; p-styrenesulfonic acid, sodium salt; ethylenesulfonic acid, sodium salt; 2-sulfoethyl methacrylate, sodium salt; 2-sulfoethyl methacrylate, 3-acryloyloxypropane-1-sulfonic acid, sodium salt; 2-sulfobutyl methacrylate, sodium salt; 4-sulfobutyl methacrylate, sodium salt; N-(2-methacryloyloxy) ethylsulfate and glyceryl methacrylate.

Representative group (I) polymers include:

1. Poly(N-isopropylacrylamide-co-sodium 2-acrylamido-2-methylpropanesulfonate-co-N,N'-methylenebisacrylamide) (weight ratio 80/10/10).

2. Poly(N-isopropylacrylamide-co-methacrylic acid-co-N,N'-methylenebisacrylamide) (weight ratio 80/10/10).

3. Poly(N-isopropylacrylamide-co-2-hydroxyethyl methacrylate-co-N,N'-methylenebisacrylamide) (weight ratio 85/5/10).

4, 5, 6, 7, 8. Poly(N-isopropylacrylamide-co-2-hydroxyethyl methacrylate-co-sodium 2-acrylamido-2-methylpropanesulfonate-co-N,N'-methylenebisacrylamide) having the following weight ratios:

| Polymer | Weight Ratio |
|---------|--------------|
| 4 | 80/5/5/10 |
| 5 | 83/5/2.5/9.5 |
| 6 | 84.5/5/0.5/10 |
| 7 | 83/5/2/10 |
| 8 | 80.9/4.8/4.8/9.5 |

It is an advantage of the group (I) polymers having the sulfonate salt groups that they have sufficient hydrophilicity so that they can be prepared without the presence of surfactants, which can be detrimental to the activity of the enzymes and/or antibodies coated in the assay elements. When surfactants are used in the polymerization process, they can be present from 0 up to about 9% of the polymerization mixture.

Representative monomers for forming the water-soluble vinyl addition copolymers of group (VI) are selected from the group consisting of 2-acrylamido- 2-methylpropanesulfonic acid, sodium salt; o- and p-styrenesulfonic acid, potassium salt; p-styrenesulfonic acid, potassium salt; p-styrenesulfonic acid, sodium salt; ethylenesulfonic acid, sodium salt; 2-Sulfoethyl methacrylate, sodium salt; 2-sulfoethyl methacrylate; 3-acryloyloxypropane-1-sulfonic acid, sodium salt, 3-methacryloyloxypropane-1-sulfonic acid, sodium salt; 3-sulfobutyl methacrylate, sodium salt; 4-sulfobutyl methacrylate, sodium salt; N-(2-sulfo-1,1-dimethylethyl)acrylamide, potassium salt; and sodium 2-methacryloyloxyethylsulfate. Poly(N-isopropylacryl-amide-co-sodium 2-acrylamido-2-methylpropanesulfonate) (weight ratio 85/15) are particularly useful.

The support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

The layers forming the elements used in the following examples were prepared using the following procedure. Each layer was dried before it was overcoated with another layer.

1. Coating the a cross-linked gelatin layer on subbed poly(ethylene terephthalate) support. The coating composition contained gelatin and an electron transfer agent [e.g., 4'-hydroxyacetanilide (4'-HA)], a buffer, surfactant, and a gelatin hardener.
2. Coating the receptor zone. The coating composition for the zone contains an antibody for the analyte (ligand) immobilized on 0.1–5 mm polymer beads in a polymer. In some examples the zone includes a dye, buffer and surfactant.
3. Coating the bead spreading layer over the dried receptor zone. The coating composition contained large (20–35 mm) polymer particles or beads [typically poly(vinyltoluene-co-methacrylic acid) (weight ratio 98/2) beads] adhered together with a latex polymer adhesive, preferably poly(methyl acrylate-co-sodium 2-acrylamido-2-methylpropane-sulfonate-co-2-acetoacetoxyethyl methacrylate) (weight ratio 90/4/6). The layer may include a leuco dye, an electron transfer agent, dimedone, a buffer, bovine serum albumin, and a surfactant.
4. A horseradish peroxidase, usually amine-enriched horseradish peroxidase, labeled analyte composition is gravure coated on top of the bead spreading layer. The composition optionally can include an electron transfer agent (4'-HA), a buffer (MOPS), bovine serum albumin, and a hydrophilic polymer vehicle such as polyacrylamide.

The following examples illustrate the practice of this invention.

EXAMPLE 1-Preparation of a Leuco Dye/Antioxidant Stable Coating Composition

Part I: Preconditioning of Grinding Media

A 4.0 L glass bottle was charged with 2200 cc of zirconium oxide grinding spheres having an average diameter of 1 mm (Zirbeads XR sold by Zircoa Inc.) and 1600 cc of 1N sulfuric acid, capped and rolled at 50% of the critical speed for 12 hours. The acidic solution was separated from the grinding beads through a retaining screen, and the beads were washed on a vibrating screen with a continuous spray of water to remove residual acid and undersized media fragments and then dried in a convection oven to remove moisture.

Part II: Preparation of Slurry to be Milled

A mixture of the following composition was prepared:

|  | Weight | Wet (%) | Dry (%) |
|---|---|---|---|
| 4,5-Bis(4-dimethylaminophenyl)-2-(3,5-dimethoxy-4-hydroxyphenyl)imidazole Leuco Dye | 49.50 | 4.8 | 68 |
| Dimedone (5,5-dimethyl-1,3-cyclohexanedione) Antioxidant | 12.38 | 1.2 | 17 |
| Tetronic 908 (83% active) | 8.95 | 0.73 | 10 |
| Surfactant 10G (10% solution in water) | 37.12 (3.712 dry) | 0.004 | 5 |
| Water | 882.05 | Balance | — |

Part III: Milling Process

A 2.5 L glass vessel is charged with 1375 cc of the dry conditioned beads prepared in Part I and the slurry prepared in Part II, then is purged with nitrogen gas to blanket the vessel and minimize air oxidation of the dye, capped, and placed on a conventional roller mill. The drive roller speed is set to achieve a rotational speed of 60% of the vessel's critical speed (70.4 rpm measured with a conventional tachometer). After 5 days, the milling is stopped and the media separated by pouring the composition through a screen having openings of 0.2 mm average diameter. The collected stable dye/antioxidant coating composition is again blanketed with nitrogen for storage before formulating the final coating composition. The major portion of the particles had a particle size of the solids in the coating composition of about 300 to 600 nm measured by light scattering with a Microtrac Particle Analyzer.

EXAMPLE 2

In this example a prior art leuco dye coating composition is compared to a coating composition prepared according to the present invention. The comparison is carried out with a multilayer dry immunoassay element in an assay for digoxin. The leuco dye coating composition prepared according to this invention was incorporated in a receptor zone located at an interphase between the element's spreading layer and a cross-linked hydrophilic layer. The prior art coating composition was incorporated into the spreading layer of a control element described below. A schematic of the element is presented hereinafter.

Procedure:

Two sets of elements were prepared. First a control element wherein the leuco dye was incorporated into the spreading layer by conventional procedures using dimethyl sulfoxide. Secondly an element in which the dye coating composition was prepared as described in Example 1 is coated with receptor into the above described receptor zone. The coating composition had the following concentrations when milled:

| | |
|---|---|
| Leuco Dye (same as Ex. 1) | 5% |
| Dimedone | 1.25% |
| Tetronic 908 (83% Active) | 0.50% |
| Surfactant 10G | 0.25% |

The resulting milled dye coating composition was added to an aqueous coating composition of the other ingredients of the receptor layer. The bead spreading layer contained additional dimedone. The dye was incorporated in the control element by dissolving the dye (9.76%) and dimedone (2.44%) in dimethyl sulfoxide and adding the solution to a well-stirred aqueous coating composition of the remaining ingredients of the bead spreading layer, which also included additional dimedone, causing precipitation of the dye and formation of an aqueous dye coating composition.

Attempts to incorporate the above DMSO/dye/dimedone solution into the receptor zone resulted in an agglomerated, uncoatable receptor layer coating composition. This coating composition had to be incorporated in the spreading layer of the control. The control and experimental coating compositions were coated as the bead spreading layer, and the separate receptor layer, respectively, with the other required layers of test elements designed for assay of digoxin. The final elements had the configurations and coating compositions shown in FIGS. 1 (control) and 2 (experiment). These were cut and mounted in slide mounts for processing.

The prepared control element and the element of the invention had the configuration and ingredient concentrations presented in FIGS. 1 and 2 below.

FIG. 1
Control (Example 2)

| Layer | Wet Coverage (g/m$^2$) | Components | Dry Coverage (g/m$^2$) |
|---|---|---|---|
| Labeled Ligand Layer | 4.3 | DI Water | |
| | | Digoxin-HRP | 0.000012 |
| | | MOPS, pH 7.0 | 0.0045 |
| | | Bovine Serum Albumin | 0.000215 |
| | | Polyacrylamide | 0.00108 |
| | | 4'-Hydroxyacetanilide | 0.000325 |
| | | Magenta Dye | 0.0269 |
| Bead Spreading Layer | 270 | DI Water | |
| | | TES, pH 7.0 | 0.219 |
| | | Dimedone | 0.50 |
| | | Triarylimidazole Leuco Dye | 0.2 |
| | | Dimethyl Sulfoxide | 1.8 |
| | | 4'-Hydroxyacetanilide | 0.45 |

FIG. 1
Control (Example 2)

| Layer | Wet Coverage (g/m$^2$) | Components | Dry Coverage (g/m$^2$) |
|---|---|---|---|
| | | Bovine Serum Albumin | 1.0 |
| | | Mannitol | 1.0 |
| | | Glycerol | 2.0 |
| | | Adhesive Polymer | 2.583 |
| | | Polymer Beads (30 μm) | 130 |
| Receptor Zone | 45 | DI Water | |
| | | Polymer Binder | 0.60 |
| | | TES, pH 7.0 | 0.1 |
| | | TX-100 | 0.02 |
| | | Antibody Polymer A Particles (0.5 μm) | 0.015 |
| Gelatin Layer | 100 | DI Water | |
| | | Gelatin | 10 |
| | | TES, pH 7.0 | 4.58 |
| | | 4'-Hydroxyacetanilide | 0.30 |
| | | TX-100 | 0.02 |
| | | Hardener | 0.15 |
| | | Poly(ethylene terephthalate) support | |

FIG. 2
(Example 2)—Invention: Dye coating composition in the Receptor

| Layer | Wet Coverage (g/m$^2$) | Components | Dry Coverage (g/m$^2$) |
|---|---|---|---|
| Labeled Ligand Layer | 4.3 | DI Water | |
| | | Digoxin-HRP | 0.000012 |
| | | MOPS, pH 7.0 | 0.0045 |
| | | Bovine Serum Albumin | 0.000215 |
| | | Polyacrylamide | 0.00108 |
| | | 4'-Hydroxyacetanilide | 0.000325 |
| | | Magenta Dye | 0.0269 |
| Bead Spreading Layer | 270 | DI Water | |
| | | TES, pH 7.0 | 0.219 |
| | | Dimedone | 0.45 |
| | | 4'-Hydroxyacetanilide | 0.45 |
| | | Bovine Serum Albumin | 1.0 |
| | | Mannitol | 1.0 |
| | | Glycerol | 2.0 |
| | | Adhesive Polymer | 2.583 |
| | | Polymer Beads (30 μm) | 130 |
| Receptor Zone | 45 | DI Water | |
| | | Polymer Binder | 0.45 |
| | | Triarylimidazole Leuco Dye | 0.2 |
| | | Dimedone | 0.05 |
| | | Tetronic 908 | 0.02 |
| | | Surfactant 10G | 0.01 |
| | | TES, pH 7.0 | 0.1 |
| | | TX-100 | 0.02 |
| | | Antibody Polymer A Particles (0.5 μm) | 0.015 |
| Gelatin Layer | 100 | DI Water | |
| | | Gelatin | 10 |
| | | TES, pH 7.0 | 4.58 |
| | | 4'-Hydroxyacetanilide | 0.30 |
| | | TX-100 | 0.02 |
| | | Hardener | 0.15 |
| | | Poly(ethylene terephthalate) support | |

The names and symbols in the elements of FIGS. 1 and 2, and of FIG. 3, infra. have the following meanings.
DMSO: Dimethyl sulfoxide
DI Water: Distilled deionized water Digoxin-Horseradish
Peroxidase (HRP): A conjugate of digoxin and horseradish peroxidase
MOPS: Morpholinopropanesulfonic acid buffer
TES: N-[Tris(hydroxymethyl)methyl]-2-aminoethanesulfonic acid buffer
Dimedone: 5,5-Dimethyl-1,3-cyclohexanedione
Triarylimidazole Leuco Dye: 4,5-Bis(4-dimethylaminophenyl)-2-(3,5-dimethoxy-4-hydroxyphenyl)imidazole blue forming leuco dye
Zonyl FSN: A nonionic, fluorinated surfactant sold by dupont de Nemours
Polymer adhesive: Poly(methyl acrylate-co-sodium 2-acrylamido-2-methylpropanesulfonate-co-2-acetoacetoxyethyl methacrylate)
Polymer beads: Poly(m-&p-vinyltoluene-co-methacrylic acid)
Antibody-Polymer A Particles: Poly[styrene-co-p-(2-chloroethylsulfonylmethyl)-styrene] polymer particles with antibody covalently bound thereto
Antibody-Polymer B Particles: Poly[styrene-co-3-(p-vinylbenzylthio)propionic acid] polymer particles with antibody covalently bound thereto
Hardener: Bis(vinylsulfonylmethyl) ether gelatin hardener
TX-100: Triton X-100, an octylphenoxy polyethoxy ethanol nonionic surfactant sold by Rohm and Haas
Tetronic 908: A poly[poly(ethylene oxide)-block-poly(propylene oxide)] block copolymer sold by BASF
Surfactant 10G: An isononylphenoxypolyglycidol surfactant sold by Olin Chem Co. having about 10 polymerized glycidol units
Magenta dye: 4,5-Dihydroxy-3-(6,8-disulfo-2-naphthylazo)-2,7-naphthalenedisulfonic acid, sodium salt
Polymer binder: Poly(N-isopropylacrylamide-co-methacrylic acid-co-N,N'-methylenebisacrylamide) (weight ratio 80/10/10)

Each element was spotted with 11 mL of serum containing either 0 or 6 ng/mL of digoxin, then incubated at 37° C. for 5 min. The elements were removed from the incubator and washed with 12 mL of wash fluid having the following composition:

| Hydrogen peroxide (HRP) | 0.03% |
|---|---|
| 4'-Hydroxyacetanilide (4'-HA) | 5 mM |
| Diethylenetriaminepentaacetic acid (DTPA) | 10 µM |
| Sodium phosphate buffer (pH 6.8) | 0.01 M |
| Hexadecylpyridinium chloride | 0.1% |

After washing, the elements were placed again in an incubator at 37° C., and the rate of leuco dye oxidation was measured at 670 nm by reflectance densitometry. The results provided in Table I show improved sensitivity and reduced imprecision, i.e., the difference between the rates with no digoxin and with 6 ng/mL of digoxin is the rate range, and the wider the range, the greater the sensitivity. The imprecision was measured as a percent coefficient of variance, the lower the variance, the lower the imprecision. N is the number of replications (the rate range and imprecision are the means for this number of replications).

TABLE I

| Dye Composition | Rate Range (Sensitivity) | Imprecision (% CV) | N |
|---|---|---|---|
| Control | 0.0603 | 0.00162 | 10 |
| Invention | 0.0807 | 0.00128 | 10 |

TABLE I-continued

| Dye Composition | Rate Range (Sensitivity) | Imprecision (% CV) | N |
|---|---|---|---|
| % Change | 34% Increase | 21% Decrease | |

Comparative Example 3-Comparison of Dye coating composition Methods in a Digoxin Assay Element Another dye coating composition was prepared as described in Example 1 except using a 0.952% of Alkanol XC, a sodium alkyl naphthalene sulfonate anionic surfactant sold by dupont Chem. Co., in place of the combination of surfactants of the invention, i.e., the Tetronic 908 and Surfactant 10G. The coating composition was incorporated in the spreading layer of a control digoxin assay element by the same technique used in preparing the control in Example 2, wherein the bead spreading layer was also the receptor layer. A control element was also prepared similar to that described in Example 2 using a DMSO solution. The configuration and coating composition of both are provided in FIG. 3. Elements prepared from the coatings were made and tested as described for Example 2, and the results are provided in Table II. As in Example 2, the test elements of the invention made from the milled coating composition had greater sensitivity and lower imprecision than those made from the DMSO coating composition; however, the milled coating composition (free of the surfactant/stabilizer combination of the invention), which was coated immediately after preparation, was unstable and settled out in about 24 hours. This is unsuitable for production scale manufacturing. In contrast, the coating composition of the invention prepared in Example 2 was stable for over 2 weeks.

TABLE II

| Dye Composition | Rate Range (Sensitivity) | Imprecision (% CV) | N |
|---|---|---|---|
| Control | 0.037 | 0.00127 | 10 |
| Invention | 0.045 | 0.000816 | 10 |
| % Change | 22% Increase | 36% Decrease | |

FIG. 3
Elements for Example 3

| Layer | Wet Coverage (g/m²) | Components | Dry Coverage (g/m²) Dye coating composition | |
|---|---|---|---|---|
| | | | DMSO | Invention |
| Labeled Ligand Layer) | 4.3 | DI Water | | |
| | | Digoxin-HRP | 0.000012 | 0.000012 |
| | | MOPS, pH 7.0 | 0.0045 | 0.0045 |
| | | Bovine Serum Albumin | 0.000215 | 0.000215 |
| | | Polyacrylamide | 0.00108 | 0.00108 |
| | | 4'-Hydroxyacetanilide | 0.000325 | 0.000325 |
| Bead spreading Layer | 270 | DI Water | | |
| | | TES, pH 7.0 | 0.219 | 0.219 |
| | | Dimedone | 0.5 | 0.5 |
| | | Triarylimidazole Leuco Dye | 0.2 | 0.2 |
| | | Alkanol XC | 0.0 | 0.038 |
| | | Dimethyl Sulfoxide | 1.8 | 0 |
| | | 4'-Hydroxyacetanilide | 0.15 | 0.15 |
| | | Zonyl FSN | 0.054 | 0.057 |

TABLE II-continued

|  | Component | | |
|---|---|---|---|
|  | Polymer Adhesive | 2.583 | 2.583 |
|  | Polymer Beads (30 µm) | 130 | 130 |
|  | Potassium Phosphate, pH 7.0 | 0.039 | 0.039 |
|  | Antibody Polymer B Particles | 0.010 | 0.010 |
| Gelatin 100 | DI Water | | |
|  | Gelatin | 10 | 10 |
|  | TES, pH 7.0 | 4.58 | 4.58 |
|  | 4'-Hydroxyacetanilide | 0.30 | 0.15 |
|  | TX-100 | 0.02 | 0.02 |
|  | Hardener | 0.15 | 0.15 |
|  | Poly(ethylene terephthalate) support | | |

The invention has been described in detail with particular reference to preferred embodiments thereof, but it will be understood that variations and modifications can be effected within the spirit and scope of the invention.

We claim:

1. A dry immunoassay analytical element for determining a ligand comprising:

(i) a receptor capable of specifically binding a member selected from the group consisting of the ligand, a ligand analog and a specific binder which specifically binds to the ligand and the ligand analog; and (ii) at least one layer comprising a leuco dye composition comprising:

| | Component | Dry Weight Ratio w/v % |
|---|---|---|
| a) | triarylimidazole leuco dye | 55–80 |
| b) | antioxidant | 7–40 |
| c) | poly[poly(ethylene oxide)-block-poly(propylene oxide)] nonionic block copolymer | 6–20 |
| d) | alkylaryloxypoly(alkylene oxide) nonionic surfactant | 1–16 |

2. A dry immunoassay analytical element for determining a ligand comprising, in the following order:

(A) a layer containing a labeled immunoreagent comprising a label conjugated to the ligand or a ligand analog thereof;

(B) a spreading layer comprising a bead matrix;

(C) a receptor layer comprising (i) a fixed concentration of a receptor capable of specifically binding the labeled immunoreagent, wherein the receptor is covalently bonded to polymeric beads that are smaller than the beads in layer (B), and (ii) a leuco dye composition comprising

| | Component | Dry Weight Ratio w/v % |
|---|---|---|
| a) | triarylimidazole leuco dye | 55–80 |
| b) | antioxidant | 7–40 |
| c) | poly[poly(ethylene oxide)-block-poly(propylene oxide)] nonionic block copolymer | 6–20 |
| d) | alkylaryloxypoly(alkylene oxide) nonionic surfactant | 1–16 |

(D) a cross-linked hydrophilic polymer layer; and, (E) a support;

wherein the label is capable of reacting directly or indirectly with the leuco dye composition to generate a detectable dye.

3. A dry immunoassay analytical element for determining a ligand comprising, in the following order:

(A) a layer containing a labeled immunoreagent comprising a label conjugated to the ligand or a ligand analog thereof;

(B) a spreading layer comprising a bead matrix;

(C) a cross-linked polymer layer; and (D) a support;

wherein the spreading layer (B) comprises:

(i) beads having a size in the range of 20–35 µm;

(ii) a fixed concentration of a receptor capable of specifically binding the labeled immunoreagent, wherein the receptor is covalently bonded to polymeric beads that are (a) smaller than the beads comprising the matrix of layer (B)(i) and (b) are immobilized within the bead matrix of layer (B); and, (iii) a leuco dye composition comprising:

| | Component | Dry Weight Ratio w/v % |
|---|---|---|
| a) | triarylimidazole leuco dye | 55–80 |
| b) | antioxidant | 7–40 |
| c) | poly[poly(ethylene oxide)-block-poly(propylene oxide)] nonionic block copolymer | 6–20 |
| d) | alkylaryloxypoly(alkylene oxide) nonionic surfactant | 1–16 | wherein the label is capable of reacting directly or indirectly with the leuco dye composition to generate a detectable dye.

4. The element of any one of claims 1, 2 or 10 wherein the leuco dye is 4,5-bis(4-dimethylaminophenyl)-2-(3,5-dimethyloxy-4-hydroxyphenyl) imidazole.

5. The element of any one of claims 1, 2 or 3 wherein the antioxidant is dimedone, and the nonionic surfactant is an isononylphenoxypoly(glycidol) having about 10 recurring polymerized glycidol units.

6. The element of any one of claims 1, 2 or 3 wherein the leuco dye is 4,5-bis(4-dimthylaminophenyl)-2-(3,5-dimethyloxy-4-hydroxyphenyl)imidazole; the antioxidant is dimedone; and the nonionic surfactant is an isononylphenoxypoly(glycidol) having about 10 recurring polymerized glycidol units.

7. A method for determining a ligand in an aqueous liquid sample, comprising the steps of:

A. providing the dry immunoassay analytical element of claim 2 or 3, wherein the label is an enzyme;

B. contacting a finite area of the layer comprising the labeled immunoreagent with a sample of the liquid sample thereby forming an immobilized labeled immunoreagent-receptor complex;

C. contacting the immobilized labeled immunoreagent-receptor complex with a solution of substrate for the enzyme thereby catalyzing the generation of the detectable dye from the leuco dye composition; and D. measuring the amount of the detectable dye generated to determine the concentration of the ligand in the aqueous liquid sample.

* * * * *